United States Patent
Avadhani et al.

(10) Patent No.: US 6,255,439 B1
(45) Date of Patent: Jul. 3, 2001

(54) 1,1-BIS(4-HYDROXYPHENYL)-3-ALKYLCYCLOHEXANES, METHOD FOR THEIR PREPARATION AND POLYCARBONATES PREPARED THEREFROM

(75) Inventors: Chilukuri Ver Avadhani; Prakash Purushottam Wadgaonkar; Swaminathan Sivaram, all of Pune (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/652,185

(22) Filed: Aug. 31, 2000

(51) Int. Cl.[7] .................................................. C08G 64/00
(52) U.S. Cl. ............................ 528/196; 528/198; 568/816
(58) Field of Search ............................ 568/816; 528/196, 528/198

(56) References Cited

U.S. PATENT DOCUMENTS 4,503,273  3/1985  Mozdzen ............................ 568/816

FOREIGN PATENT DOCUMENTS 78216  8/1961  (IN).

OTHER PUBLICATIONS

S.C. Sethi and B.C. Subba Rao, "Cis–&Trans–3–Pentadecylcyclohexanols," *Indian Journal of Chemistry*. vol. 2, pp. 178–181 (1964) (No month).

V. Madhusudhan et al. "Catalytic Hydrogenation of Cardanol: Part I —Laboratory Scale Studies," *Indian Journal of Technology*, vol. 11, pp. 347–350 (1973) (No month).

*Primary Examiner*—Terressa M. Boykin
(74) *Attorney, Agent, or Firm*—S. Bruce Brown; Noreen C. Johnson

(57) ABSTRACT

1,1-Bis(4-hydroxyphenyl)-3-alkylcyclohexanes, as illustrated by 1,1-bis (4-hydroxyphenyl)-3-pentadecylcyclohexane, are prepared by hydrogenating a composition comprising 3-alkylphenols to the corresponding cyclohexanol, oxidizing the cyclohexanol to a cyclohexanone and contacting the cyclohexanone with phenol in the presence of an acidic catalyst. The preferred 3-alkylphenols are those derived from cashew nut shell liquid. The products can be used to prepare polycarbonates.

21 Claims, No Drawings

1,1-BIS(4-HYDROXYPHENYL)-3-ALKYLCYCLOHEXANES, METHOD FOR THEIR PREPARATION AND POLYCARBONATES PREPARED THEREFROM

BACKGROUND OF THE INVENTION

This invention relates to bisphenols and polycarbonates derived therefrom. More particularly, it relates to bisphenols of the type which may be prepared from cashew nut shell liquid.

Cashew nut shell liquid (hereinafter sometimes simply "CNSL" for brevity) has been known for years to contain compounds useful in various aspects of chemical industry, with particular reference to plastics production. It is of such interest for various purposes that technical grade distilled CNSL is a commercially available product. It comprises, in major proportion (typically about 80% by weight), a material also sold separately under the trade name CARDANOL which is a mixture of the hydroxyalkylphenols 3-(pentadec-8-enyl)phenol, 3-(pentadeca-8,11-dienyl)phenol and 3-(pentadeca-8,11,14-trienyl)phenol. Minor constituents include about 18% of a material also sold separately under the trade name CARDOL, which is a mixture of the corresponding 5-substituted resorcinols, and about 2% 2-methylcardol, which is a mixture of the corresponding 2-methyl-5-substituted resorcinols, and other materials not fully identified.

Aromatic polycarbonates are a widely used class of generally amorphous polymers characterized by such properties as transparency, durability, high impact resistance and solvent resistance. In recent years, they have been used advantageously for the fabrication of optical recording media, as exemplified by compact disks. It is very advantageous, however, to use for this purpose polycarbonates having very low birefringence values. This frequently involves the incorporation of copolymer units in a conventional polycarbonate, such as one derived from 2,2-bis(4-hydroxyphenyl)propane also known as "bisphenol A", since the birefringence values of bisphenol A homopolycarbonates are higher than is desirable.

Among the dihydroxyaromatic compounds reported to form homo- or copolycarbonates with low birefringence are 6,6'-dihydroxy-3,3,3',3'-tetramethyl-1,1'-spiro (bis)indane ("SBI"), 2,2-bis(3-methyl4-hydroxyphenyl)propane, 1,1-bis (4-hydroxyphenyl) cyclohexane, 1,1-bis(4-hydroxyphenyl)-3,3,5-trimethylcyclohexane and 1,3-bis[2-(4-hydroxyphenyl)-2-propyl]benzene, also known as 4,4'-(m-phenylenediisopropylidene) diphenol. However, problems arise in the synthesis and use of these compounds. For example, SBI is somewhat costly to produce and affords brittle polymers, and various others of these rather exotic bisphenols are produced only at considerable expense.

It is of interest, therefore, to develop new bisphenols having the potential of affording polycarbonates with high processability and low birefringence. It is of particular interest to develop bisphenols which may be easily and cheaply obtained from readily available and renewable resource materials such as CNSL.

SUMMARY OF THE INVENTION

The present invention provides a class of novel 1,1-bis(4-hydroxyphenyl)-3-alkylcyclohexanes, some of which are available from naturally occurring materials with particular reference to CNSL. Also provided is a method for preparing said 1,1- bis(4-hydroxyphenyl)-3-alkycyclohexanes and polycarbonates capable of production therefrom.

In one of its aspects, the invention includes 1,1- bis(4-hydroxyphenyl)-3-alkylcyclohexane compounds having the formula

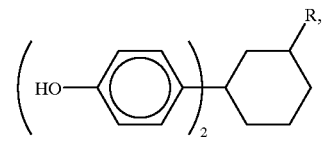

(I)

wherein R is an alkyl radical containing at least 10 carbon atoms.

Another aspect of the invention is a method for preparing such 1,1-bis (4-hydroxyphenyl)-3-alkylcyclohexanes which comprises:

(A) hydrogenating a composition comprising substituted phenols of the formula

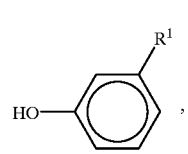

(II)

wherein $R^1$ is an alkyl or alkenyl radical containing at least 10 carbon atoms, to the corresponding substituted cyclohexanols;

(B) oxidizing said substituted cyclohexanols to the corresponding substituted cyclohexanones; and (C) contacting said substituted cyclohexanones with phenol in the presence of an acidic catalyst.

Still another aspect of the invention is polycarbonates comprising structural units derived from said 1,1- bis(4-hydroxyphenyl)-3-alkylcyclohexanes.

DETAILED DESCRIPTION OF PREFERRED EMBODIMENTS

In the 1,1- bis(4-hydroxyphenyl)-3-alkylcyclohexanes (hereinafter sometimes simply "cyclohexane bisphenols") of formula I, the R value is an alkyl radical containing at least 10, preferably from 10 to about 30, carbon atoms. Normal alkyl radicals are particularly preferred. Most preferred, by reason of its availability in CNSL, is the n-pentadecyl ($C_{15}H_{31}$) radical.

Step A of the method of the invention comprises hydrogenation of a composition comprising substituted phenols of formula II. The $R^1$ radical therein may be an alkyl or alkenyl radical, the latter being converted by hydrogenation to the corresponding alkyl radical concurrently with the hydrogenation of the aromatic ring. In a preferred embodiment, the composition being hydrogenated is at least one component of CNSL, particularly one or more of the CARDANOL components or hydrogenation products thereof and especially 3-pentadecylphenol. Thus, $R^1$ is preferably pentadecyl or a $C_{15}$ mono-, di- or triolefinic radical, or a mixture of any of these.

3-Pentadecylphenol may be prepared by hydrogenation of the CARDANOL composition or constituents thereof, and is commercially available as so prepared from Cardolite Corp. Typical hydrogenation conditions may include temperatures in the range of about 140–160° C., pressures in the range of about 0.5–1.52 megapascals (MPa) and the presence of a catalyst, typically a Group VIII metal catalyst such as Raney nickel. Suitable conditions are disclosed, for example, in Indian patent specification 78,216 and in Madhusudhan et al., *Indian Journal of Technology,* 1973, 347–350, the disclosures of which are incorporated by reference herein.

Any hydrogenation conditions effective to saturate an aromatic radical may be employed in step A. Typical conditions include the presence of catalysts, especially Group VIII metal catalysts such as nickel or supported ruthenium, suitable supports including carbon, silica, alumina, silica-alurnina, aluminum phosphate, calcium phosphate, zinc aluminate and zinc titanate. The reaction may be conducted in the absence of a solvent or in the presence of at least one suitable solvent. Suitable solvents include, but are not limited to, alcohols such as methanol, isopropanol, isobutanol; ethers such as diglyme, monoglyme, 2-ethoxyethanol; and hydrocarbons such as decalin. Other conditions, including temperatures and pressures, may vary with the catalyst employed and can be determined by simple experimentation. For such catalysts as Raney nickel and ruthenium on carbon, pressures in the range of about 0.5–16.2 MPa, preferably about 2–15.2 MPa, and more preferably about 5–15.2 MPa, and temperatures in the range of about 150–280° C. and preferably about 175–250° C. are typical. As noted hereinabove, some of the same catalysts may be used to reduce the CARDANOL constituents to pentadecylphenol under somewhat milder conditions, particularly lower temperatures. Illustrative of conditions for the hydrogenation of step A are the aforementioned Indian patent specification 78,216, as well as U.S. Pat. No. 4,503,273 and Sethi et al., *Indian Journal of Chemistry,* 1964, 178–181, the disclosures of which are incorporated by reference herein.

In step B, the substituted cyclohexanol produced in step A is oxidized to the corresponding cyclohexanone. The oxidizing agent employed may be any such agent capable of oxidizing the hydroxy radical to a ketone carbonyl group. Typical oxidizing agents and conditions are in many standard reference works, including Advanced Organic Chemistry Reactions, Mechanisms, and Structures by Jerry March, 4th edition, John Wiley & Sons, 1992. Mustrative oxidizing agents are hexavalent chromium compounds such as sodium dichromate and pyridinium chlorochromate, hypochlorites such as calcium hypochlorite, peroxides such as hydrogen peroxide and t-butyl hydroperoxide, and molecular oxygen, optionally activated by microwave radiation or the like. Alkali metal dichromates such as sodium dichromates are particularly useful in an acidic medium such as acetic acid.

Reaction temperatures in step B will depend on the oxidizing agent employed. For hexavalent chromium compounds, temperatures in the range of about 0–100° C. and preferably about 35–80° C. are typical. The amount of oxidizing agent is most often a slight excess over the stoichiometric amount, typically about a 10–25% excess.

Finally, in step C the cyclohexanone product of step B is contacted, under reaction-producing conditions, with a phenolic compound, typically unsubstituted phenol. Such conditions include the presence of an acidic catalyst, as illustrated by ion exchange resins in the acid form, acidic clays, sulfated zirconia and excess anhydrous hydrogen chloride, the latter preferably being used in combination with a mercaptan such as mercaptopropionic acid. Temperatures in the range of about 10–40° C. are typical. The intermediates and product formed in each of steps A–C may be worked up and isolated by conventional means. These may include solvent removal when a solvent is employed, washing, drying and recrystallization.

The polycarbonates of this invention may be prepared by conventional polycarbonate synthesis methods such as interfacial, transesterification and redistribution methods, or by solid state polymerization as described, for example, in U.S. Pat. Nos. 4,948,871, 5,204,377, 5,266,659 and 5,288,838, the disclosures of which are incorporated by reference herein. All of these methods are the subject of many issued patents and publications, and need not be described in detail herein. Ester units may be incorporated in the polycarbonate by the use of a corresponding dicarboxylic acid or acid chloride in an interfacial procedure or the use of a dialkyl or diaryl, most often a diphenyl, ester of said acid in a melt or solid state procedure.

The polycarbonates of the invention include both homopolycarbonates and copolycarbonates. The copolycarbonates may also contain units corresponding to the dihydroxy compounds disclosed by name or formula (generic or specific) in U.S. Pat. No. 4,217,438, the disclosure of which is incorporated by reference herein. Such copolycarbonates typically comprise about 5–95% by number of units derived from the 1,1-bis(4-hydroxyphenyl)-3-alkylcyclohexanes of the invention, with the balance being other units.

Said other units include those having the formula

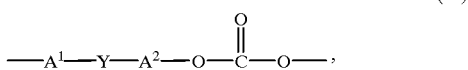

(III)

wherein each of $A^1$ and $A^2$ is a monocyclic divalent aromatic radical and Y is a bridging radical in which one or two atoms separate $A^1$ from $A^2$. The free valence bonds in formula m are usually in the meta or para positions of $A^1$ and $A^2$ in relation to Y.

The $A^1$ and $A^2$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene (alkylidene) radical. Also included, however, are unsaturated radicals and radicals which contain atoms other than carbon and hydrogen; for example, 2,2-dichloroethylidene, carbonyl, phthalidyhdene, oxy, thio, sulfoxy and sulfone. For reasons of availability and particular suitability for the purposes of this invention, the preferred units of formula m are 2,2-bis (4-phenylene)propane carbonate units, which are derived from bisphenol A and in which Y is isopropylidene and $A^1$ and $A^2$ are each p-phenylene.

The invention is illustrated by the following examples.

EXAMPLE 1

A solution of 40.35 grams (g) (130 millimoles [mmol]) of 3-pentadecylphenol prepared from CNSL in 150 milliliters (ml) of 2-propanol was charged to a 300-ml Parr reactor and 2 g of ruthenium on carbon was added. The reactor was pressurized with hydrogen at about 11 MPa and heated at 175° C. until absorption of hydrogen had ceased (about 1.5 hours). The catalyst was removed by filtration through silica gel, the solvent was stripped and the product was vacuum dried. It was the desired 3-pentadecylcyclohexanol, obtained in a yield of 40.6 g (98% of theoretical).

EXAMPLE 2

A solution of 25 g (80 mmol) of 3-pentadecylcyclohexanol in 190 ml of glacial acetic acid was cooled to about 0° C., with stirring, and a solution of 8.33 g (31.8 mmol) of sodium dichromate in 14 ml of glacial acetic acid and 5 ml of water was added dropwise over 4.5 hours at a temperature below 10° C. The reaction mixture was heated to 60° C. for one hour and vacuum stripped to remove acetic acid. The residue was diluted with water and extracted with ethyl acetate. The extract was washed with aqueous sodium bicarbonate solution and water and dried over sodium sulfate. Upon vacuum stripping of the solvent, the desired 3-pentadecylcyclohexanone was obtained as a waxy solid, m.p. 41° C. The yield was 23 g (92% of theoretical).

EXAMPLE 3

A 500-ml 3-necked flask fitted with a magnetic stirrer and gas dip tube was charged with 30 g (97 mmol) of 3-pentadecylcyclohexanone, 54.93 g (580 mmol) of phenol and 1.5 ml of mercaptopropionic acid. The resulting mixture was stirred at room temperature for 15 minutes, after which anhydrous hydrogen chloride gas was passed into the mixture for 1 hour, whereupon the mixture solidified. It was dissolved in ethyl acetate, washed with aqueous sodium bicarbonate solution and water, and dried over sodium sulfate. Vacuum stripping of solvent afforded a pink solid which was washed with petroleum ether and recrystallized from a mixture of benzene (10 parts by volume) and petroleum ether (90 parts by volume). The desired 1,1-bis(4-hydroxyphenyl)-3-pentadecylcyclohexane was obtained in a yield of 37 g (80% of theoretical); m.p. 104° C.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A 1,1- bis(4-hydroxyphenyl)-3-alkylcyclohexane compound having the formula

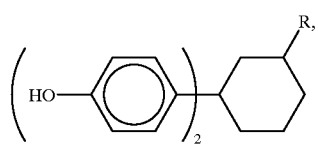

(I)

wherein R is an alkyl radical containing at least 10 carbon atoms.

2. A compound according to claim 1 wherein R is pentadecyl.

3. A method for preparing a 1,1-bis(4-hydroxyphenyl)-3-alkylcyclohexane which comprises:

(A) hydrogenating a composition comprising substituted phenols of the formula

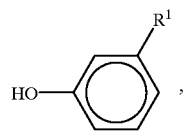

wherein $R^1$ is an alkyl or alkenyl radical containing at least 10 carbon atoms, to the corresponding substituted cyclohexanols;

(B) oxidizing said substituted cyclohexanols to the corresponding substituted cyclohexanones; and (C) contacting said substituted cyclohexanones with phenol in the presence of an acidic catalyst.

4. A method according to claim 3 wherein $R^1$ is preferably pentadecyl or a $C_{15}$ mono-, di- or triolefinic radical, or a mixture of any of these.

5. A method according to claim 4 wherein the composition of step A is prepared from cashew nut shell liquid.

6. A method according to claim 3 wherein step A is performed at a temperature in the range of about 175–250° C. and a pressure in the range of about 5–15.2 MPa, in the presence of a Group VIII metal catalyst.

7. A method according to claim 6 wherein the Group VIII metal is nickel or ruthenium.

8. A method according to claim 3 wherein the oxidizing agent in step B is a hexavalent chromium compound, a hypochlorite, a peroxide or molecular oxygen.

9. A method according to claim 8 wherein the oxidizing agent is sodium dichromate.

10. A method according to claim 9 wherein the temperature in step B is in the range of about 35–80° C.

11. A method according to claim 3 wherein the acidic catalyst in step C is an ion exchange resin in the acid form, an acidic clay, sulfated zirconia or excess anhydrous hydrogen chloride.

12. A method according to claim 11 wherein the acidic catalyst is anhydrous hydrogen chloride in combination with a mercaptan.

13. A method according to claim 12 wherein the mercaptan is mercaptopropionic acid.

14. A method according to claim 11 wherein the temperature in step C is in the range of about 10–40° C.

15. A method for preparing 1,1- bis(4-hydroxyphenyl)-3-pentadecylcyclohexane which comprises:

(A) hydrogenating, in the presence of a nickel or ruthenium catalyst, a composition comprising 3-pentadecylphenol prepared from cashew nut shell liquid to 3-pentadecylcyclohexanol;

(B) oxidizing said 3-pentadecylcyclohexanol to 3-pentadecylcyclohexanone with a hexavalent chromium compound, a hypochlorite, a peroxide or molecular oxygen; and (C) contacting said 3-pentadecylcyclohexanone with phenol in the presence of excess anhydrous hydrogen chloride in combination with a mercaptan.

16. A polycarbonate comprising structural units of the formula

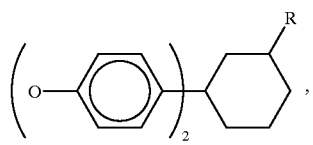

wherein R is an alkyl radical containing at least 10 carbon atoms.

17. A polycarbonate according to claim 16 wherein R is pentadecyl.

18. A polycarbonate according to claim 16 which is a homopolycarbonate.

19. A polycarbonate according to claim 16 which is a copolycarbonate.

20. A copolycarbonate according to claim 19 further comprising structural units having the formula (III)

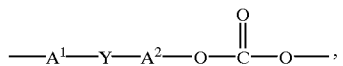

wherein each of $A^1$ and $A^2$ is a monocyclic divalent aromatic radical and Y is a bridging radical in which one or two atoms separate $A^1$ from $A^2$.

21. A copolycarbonate according to claim 20 wherein each of $A^1$ and $A^2$ is p-phenylene and Y is isopropylidene.

* * * * *